US009610017B2

(12) United States Patent
Plans Casal et al.

(10) Patent No.: US 9,610,017 B2
(45) Date of Patent: Apr. 4, 2017

(54) DEVICE AND METHOD FOR PROVIDING FEEDBACK ON BREATHING RATE

(71) Applicant: BioBeats Inc., Beverly Hills, CA (US)

(72) Inventors: David Plans Casal, Woking (GB); Christopher Turrall Clarke, Bath (GB); Paul John Leonard, Frome (GB); Ambra Dei, Leghorn (IT); Davide Morelli, Leghorn (IT)

(73) Assignee: BIOBEATS GROUP LTD (GB)

( * ) Notice: Subject to any disclaimer, the term of this patent is extended or adjusted under 35 U.S.C. 154(b) by 0 days.

(21) Appl. No.: 14/696,554

(22) Filed: Apr. 27, 2015

(65) Prior Publication Data

US 2016/0296123 A1    Oct. 13, 2016

(51) Int. Cl.
| A61B 5/02 | (2006.01) |
| A61B 5/0205 | (2006.01) |
| A61B 5/04 | (2006.01) |
| A61B 5/0452 | (2006.01) |
| A61B 5/00 | (2006.01) |

(Continued)

(52) U.S. Cl.
CPC .......... *A61B 5/0205* (2013.01); *A61B 5/0006* (2013.01); *A61B 5/0022* (2013.01); *A61B 5/0404* (2013.01); *A61B 5/044* (2013.01); *A61B 5/04017* (2013.01); *A61B 5/04085* (2013.01); *A61B 5/04525* (2013.01); *A61B 5/486* (2013.01); *A61B 5/7405* (2013.01); *A61B 5/7455* (2013.01); *A61B 5/0245* (2013.01);

(Continued)

(58) Field of Classification Search
None
See application file for complete search history.

(56) References Cited

U.S. PATENT DOCUMENTS

| 6,305,943 B1 | 10/2001 | Pougatchev et al. |
| 2006/0009698 A1* | 1/2006 | Banet ................... A61B 5/0205 600/485 |

(Continued)

FOREIGN PATENT DOCUMENTS

| CN | 204293140 U | 4/2015 |
| EP | 0875199 A1 | 11/1998 |

OTHER PUBLICATIONS

Search Report dated Jul. 1, 2016 from related Great Britain Application No. GB1506143.5, 7 pages.

*Primary Examiner* — Brian T Gedeon
*Assistant Examiner* — Ankit D Tejani
(74) *Attorney, Agent, or Firm* — Vic Lin; Innovation Capital Law Group, LLP

(57) ABSTRACT

Devices and methods for providing feedback on breathing rate are disclosed. The device comprises: a sensor interface configured to receive an electrocardiogram ECG signal; an ECG analysis unit configured to obtain a breathing rate from the received ECG signal; a feedback output mechanism for providing feedback; and a feedback generator configured to obtain an optimal breathing rate in accordance with a desired outcome and one or more heart rate and/or breathing rate characteristics detected from the ECG signal. The feedback generator is further configured to control the feedback output mechanism to output feedback synchronized to the optimal breathing rate, and subsequently adapt the feedback in accordance with changes in the one or more heart rate and/or breathing rate characteristics while the feedback is being outputted.

13 Claims, 5 Drawing Sheets

(51) Int. Cl.
  *A61B 5/044*   (2006.01)
  *A61B 5/0404*  (2006.01)
  *A61B 5/0408*  (2006.01)
  *A61B 5/0245*  (2006.01)
  *A61B 5/08*    (2006.01)
  *A61B 5/024*   (2006.01)

(52) U.S. Cl.
  CPC ........ *A61B 5/02405* (2013.01); *A61B 5/0816* (2013.01); *A61B 2560/0468* (2013.01)

(56) References Cited

U.S. PATENT DOCUMENTS

| | | |
|---|---|---|
| 2007/0299354 A1 | 12/2007 | Striepe et al. |
| 2009/0106049 A1 | 4/2009 | Breslau et al. |
| 2010/0004552 A1* | 1/2010 | Zhang .................. A61B 5/0816 600/529 |
| 2011/0015468 A1* | 1/2011 | Aarts .................. A61B 5/0205 600/26 |
| 2012/0157795 A1* | 6/2012 | Chiu .................. G06F 19/3418 600/301 |

* cited by examiner

DEVICE AND METHOD FOR PROVIDING FEEDBACK ON BREATHING RATE

CROSS-REFERENCE TO RELATED APPLICATIONS

This application claims priority to GB Patent Application No. 1506143.5, filed at the British Patent Office on Apr. 10, 2015, the disclosure of which is hereby incorporated by reference in its entirety.

TECHNICAL FIELD

The present disclosure relates to providing feedback regarding breathing rate. In particular, the present disclosure relates to providing adaptive feedback in relation to the breathing rate, based on an electrocardiogram (ECG) signal.

BACKGROUND

Breathing exercises are widely used to achieve various physiological benefits. For example, in a clinical context breathing exercises have been developed which can aid a patient in reducing their blood pressure, or assist in pain management. Breathing techniques can also help in managing stress levels.

In recent years, devices have been developed which can help a user to control their breathing in accordance with a desired breathing pattern. In one such prior art device, music is played to indicate to a user when to inhale and exhale. The device gradually prolongs the exhalation tone in a pre-programmed manner to encourage the user to slow their breathing.

The invention is made in this context.

SUMMARY

According to a first aspect of the present disclosure, there is provided a device comprising: a sensor interface configured to receive an electrocardiogram ECG signal; an ECG analysis unit configured to obtain a breathing rate from the received ECG signal; a feedback output mechanism for providing feedback; and a feedback generator configured to obtain an optimal breathing rate in accordance with a desired outcome and one or more heart rate and/or breathing rate characteristics detected from the ECG signal, control the feedback output mechanism to output feedback synchronised to the optimal breathing rate, and subsequently adapt the feedback in accordance with changes in the one or more heart rate and/or breathing rate characteristics while the feedback is being outputted.

The feedback generator can be configured to generate a feedback control signal having values ranging from a first limit to a second limit, the first limit corresponding to a defined point in an exhalation phase and the second limit corresponding to a defined point in an inhalation phase, and the feedback output mechanism can be configured to provide the feedback in accordance with the feedback control signal.

The feedback generator can be configured to: obtain a first filtered signal by applying a moving average filter with a first time window to the received ECG signal; obtain a second filtered signal by applying a moving average filter with a second time window to the received ECG signal, the second time window being longer than the first time window; obtain a difference signal by subtracting the second filtered signal from the first filtered signal; determine a maximum value and a minimum value of the difference signal within a third time window; normalise the difference signal relative to the control signal based on the determined maximum and minimum values, to obtain a normalised signal having values ranging from the first limit of the control signal to the second limit of the control signal; and obtain a performance metric based on a correlation between the normalised signal and the control signal, where the performance metric is related to how closely the breathing rate detected from the ECG signal is matched to the optimal breathing rate. The first time window can be substantially equal to 3 seconds, and/or the second time window can be substantially equal to 17 seconds.

The feedback can be configured to include cues for instructing a user when to inhale and when to exhale, in accordance with the determined optimal breathing rate.

The device can further comprise an abnormality detection mechanism configured to detect one or more predefined abnormalities based on the determined heart rate variability and/or breathing rate, and to signal a detected abnormality to the feedback generator, and the feedback generator can be further configured to obtain the optimal breathing rate in accordance with the detected abnormality.

The device may further comprise a network interface for communicating with one or more other devices over a network. In some embodiments, the abnormality detection mechanism can be configured to detect the one or more predefined abnormalities by transmitting the ECG signal to a diagnostic server via the network interface and receiving a diagnostic result indicating whether any of the predefined abnormalities were detected in the ECG signal, and/or the ECG analysis unit can be configured to obtain the breathing rate by transmitting the ECG signal to a server via the network interface, and receiving a message containing the detected breathing rate via the network interface, and/or the feedback generator can be configured to obtain the optimal breathing rate by querying a server via the network interface.

The feedback output mechanism can comprise a plurality of light sources distributed across the device, the plurality of light sources being controllable to emit visible light of different wavelengths in accordance with the generated feedback.

The feedback output mechanism can comprise a speaker for outputting an audio component of the generated feedback, and the feedback generator can be further configured to control the speaker to provide haptic feedback in the form of low-frequency audio.

The device may be configured to be held and supported by a user, and the sensor interface can comprise first and second electrocardiographic electrodes disposed on a surface of the device, the first and second electrocardiographic electrodes being arranged to detect the ECG signal when the device is held by the user. Additionally, in some embodiments the device further comprises a third electrocardiographic electrode arranged to contact both hands when the device is being held by the user, wherein the ECG analysis unit is configured to measure a reference potential from the third electrocardiographic electrode when receiving the ECG signal through the first and second electrocardiographic electrodes.

The ECG analysis unit can be configured to determine the breathing rate as being equal to a variation in peak amplitude of a pulse detected from the ECG signal.

According to a second aspect of the present disclosure, there is provided a method comprising: receiving an electrocardiogram ECG signal; obtaining a breathing rate from the received ECG signal; obtaining an optimal breathing rate in accordance with a desired outcome and one or more heart rate and/or breathing rate characteristics detected from the ECG signal; controlling a feedback output mechanism to output feedback synchronised to the optimal breathing rate; and subsequently adapting the feedback in accordance with changes in the one or more heart rate and/or breathing rate characteristics while the feedback is being outputted.

According to a third aspect of the present disclosure, there is provided a computer-readable storage medium arranged to store computer program instructions which, when executed, perform any of the methods disclosed herein.

BRIEF DESCRIPTION OF THE DRAWINGS

Embodiments will now be described, by way of example only, with reference to the accompanying drawings, in which.

DETAILED DESCRIPTION

Figure 1:
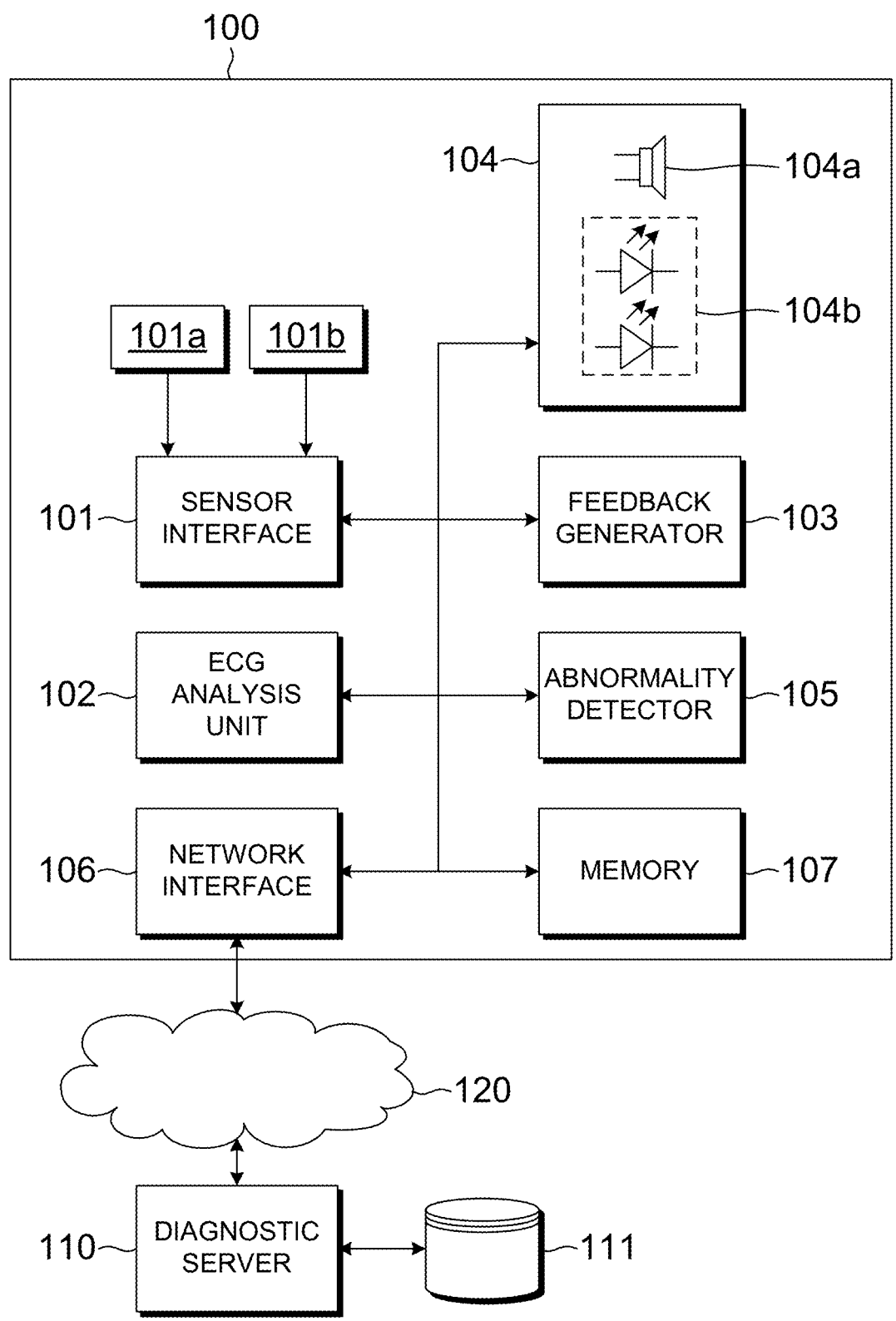
FIG. 1 schematically illustrates a device for providing feedback regarding breathing rate, according to an embodiment.

Referring now to FIG. 1, a device for providing feedback regarding breathing rate is schematically illustrated, according to an embodiment. As shown in FIG. 1, the device 100 comprises a sensor interface 101, an electrocardiogram (ECG) analysis unit 102, a feedback generator 103, a feedback output mechanism 104, an abnormality detection mechanism 105, a network interface 106, and memory 107. The memory 107 can be any type of suitable non-transitory computer readable storage medium, and is arranged to store computer program instructions which, when executed, cause the device to perform various functions as disclosed herein. The feedback output mechanism 104 is configured to provide audiovisual feedback to a user, and can include one or more audio output devices 104a and light sources 104b. In the present embodiment the feedback output mechanism includes a plurality of light emitting diodes (LEDs) 104b which can be controlled to emit light of different wavelengths.

Depending on the embodiment, certain elements shown in FIG. 1 may be implemented solely in hardware or software, or in a combination of both. For example, the feedback output mechanism 104 may include hardware components suitable for outputting audiovisual feedback, and the sensor interface 101 and network interface 102 may include physical interface components such as jacks and/or antennas. However, other elements in which processing steps are performed, including the ECG analysis unit 102, feedback generator 103 and abnormality detection mechanism 105 may be implemented in software or hardware, or as a combination.

The device 100 further comprises first and second ECG electrodes 101a, 101b through which the sensor interface 101 is configured to receive an ECG signal. In the present embodiment the ECG electrodes 101a, 101b are included in the device 100, but in other embodiments the ECG electrodes 101a, 101b may be physically separate from the device. For example, in some embodiments the sensor interface 101 may be configured to receive an ECG signal wirelessly from a remote sensor, such as a wearable chest strap ECG sensor including the ECG electrodes 101a, 101b.

The ECG analysis unit 102 can be configured to execute various analytical functions on the ECG signal received through the sensor interface 101. In the present embodiment the ECG analysis unit 102 is configured to obtain a breathing rate from the received ECG signal. In some embodiments, in addition to obtaining the breathing rate the ECG analysis unit 102 may be configured to perform other functions, for example determining heart rate variability (HRV) from the ECG signal.

In the present embodiment the ECG analysis unit 102 is configured to detect the ECG signal as a differential signal via contact between the user's hands and the first and second ECG electrodes 101a, 101b while the user is holding the device 100. The ECG analysis unit 102 of the present embodiment includes a digital gain control that allows the circuit to operate correctly over a range of input signal levels. The peak amplitude of the ECG pulses correlates with the user's breathing rate once gain control has stabilised.

In the present embodiment the ECG analysis unit 102 is configured to amplify the voltage difference between the user's hands using a multistage amplifier with bandpass filtering. The multistage amplifier includes a variable gain amplifier, and enables the ECG circuit to be adaptable over a wide range (20:1) of input signals under software and/or hardware control. For example, in the present embodiment the second stage amplifier is configured to have digitally controllable gain, and can be controlled via software or a Field Programmable Gate Array (FPGA). However, in other embodiments different methods of amplifying the ECG signal may be used, for example a single stage amplifier may be used instead of a multistage amplifier.

In the present embodiment, the amplified ECG signal is converted from analogue to digital by an analogue-to-digital converter (ADC). The digital signal can then be read into an FPGA or a processor. In the present embodiment the ADC is configured to sample the ECG signal at 200 Hertz (Hz).

In the present embodiment the ECG analysis unit 102 is further configured to determine HRV from the ECG signal, by applying filtering to remove noise and enhance the QRS part of the signal. Various algorithms for estimating heart rate based on QRS events detected from an ECG signal are known in the art, and a detailed description will not be provided here.

Although in the present embodiment the ECG analysis unit 102 is configured to determine the breathing rate as being equal to a variation in peak amplitude of a pulse detected from the ECG signal, other methods of detecting the breathing rate are known in the art, and a detailed explanation will not be provided here so as not to obscure the inventive concept. For example, the breathing rate may be determined based on other characteristics of the ECG signal, including the median or mean amplitude of the whole QRS event, or of only the negative part or positive part.

Continuing with reference to FIG. 1, the feedback generator 103 is configured to obtain an optimal breathing rate in accordance with a desired outcome and one or more heart rate and/or breathing rate characteristics detected from the ECG signal. For example, the desired outcome may be to synchronise the user's breathing pattern according to the Herbert-Benson breathing technique, or to provide pain relief by assisting the user in managing their heart rate and breathing rate, or to achieve general relaxation. The device may also be beneficial for individuals with disorders that can create anxiety or anger, such as attention deficit hyperactivity disorder (ADHD), autism or post-traumatic stress disorder (PTSD). Data captured by the device, such as the raw ECG data and information about characteristics detected from the ECG signal, may be uploaded to a server to be reviewed by a healthcare professional. A physician may then be able to adjust a patient's medication regime or other treatment in accordance with the uploaded data, for example by reducing a prescribed dosage of anti-depressants when the data indicates an improvement in the patient's ability to maintain a relaxed breathing state while using the device.

The characteristics detected from the ECG signal may include the breathing rate and/or HRV detected by the ECG analysis unit 102, and may further include other characteristics such as any abnormalities detected by the abnormality detection mechanism 105. The feedback generator 103 is further configured to control the feedback output mechanism 104 to output audiovisual feedback synchronised to the optimal breathing rate, and subsequently adapt the audiovisual feedback in accordance with changes in the one or more heart rate and/or breathing rate characteristics while the audiovisual feedback is being outputted. In some embodiments, other types of sensory feedback may also be provided in addition to audiovisual feedback. In the present embodiment, the feedback generator 103 can control the speaker 104a included in the feedback output mechanism 104 to provide haptic feedback in the form of low-frequency audio. In another embodiment, a dedicated haptic feedback mechanism may be provided.

In the present embodiment the feedback generator 103 includes an audio mixer configured to play overlapped sample streams stored in computer-readable memory. The feedback generator 103 can control the audio mixer to generate audio output with a rhythm that is synchronised to the heartbeat or breathing rate of the user. In some embodiments the generated audiovisual feedback may be configured to include specific audio and/or visual cues for instructing a user when to inhale and when to exhale, in accordance with the determined optimal breathing rate. However, in other embodiments the audiovisual feedback can be configured to increase or decrease a user's heart rate and/or breathing rate without the use of specific cues, for example by using audio and visual output that are known to be generally soothing to a user, such as subtly changing blue/green light patterns and relaxing music/sounds.

As shown in FIG. 1, the device of the present embodiment further comprises an abnormality detection mechanism 105 configured to detect one or more predefined abnormalities based on the determined heart rate variability and/or breathing rate, and to signal a detected abnormality to the feedback generator. The feedback generator can then obtain the optimal breathing rate in accordance with the detected abnormality. However, in other embodiments abnormality detection may not be performed, and accordingly the abnormality detection mechanism 105 may be omitted.

Examples of abnormalities that can be detected by the abnormality detection mechanism 105 include, but are not limited to: an indicator of high stress; atrial fibrillation; cardiomyopathy; autonomic neuropathy. In some embodiments, the device may be configured to issue an alert to the user and/or a healthcare professional in response to a certain type of abnormality being detected, such as an abnormality that may indicate a need for immediate medical attention.

As shown in FIG. 1, the device 100 further comprises a network interface 106 for communicating with one or more other devices over a network 120. Depending on the embodiment, various processing steps may be performed remotely by communicating with a suitable network device, for example a cloud server. That is, functions of the ECG analysis unit 102, feedback generator 103 and abnormality detection mechanism 105 can be performed either locally or remotely. For example, in the present embodiment the abnormality detection mechanism 105 is configured to detect the one or more predefined abnormalities by transmitting the ECG signal to a diagnostic server 110 via the network interface 106 and receiving a diagnostic result indicating whether any of the predefined abnormalities were detected in the ECG signal.

In some embodiments, a cloud server 110 may store data received from the device 100 in a database 111. For example, the server no may store a copy of the ECG signal received from the device 100, and/or information about characteristics detected from the ECG signal, such as HRV, breathing rate and any abnormalities present in the ECG signal. The information in the database in could be accessed by the user and/or health professionals at a later stage, for example in order to diagnose certain medical conditions or to monitor a patient's state during hospital waiting periods. Additionally, by storing a record of a data obtained by the device over longer time periods for a particular individual, a baseline of heart rate activity for the individual can be obtained. Certain conditions may be diagnosed by detecting a significant variation from the baseline, for example a substantial change in HRV or vagal balance.

Figure 2:
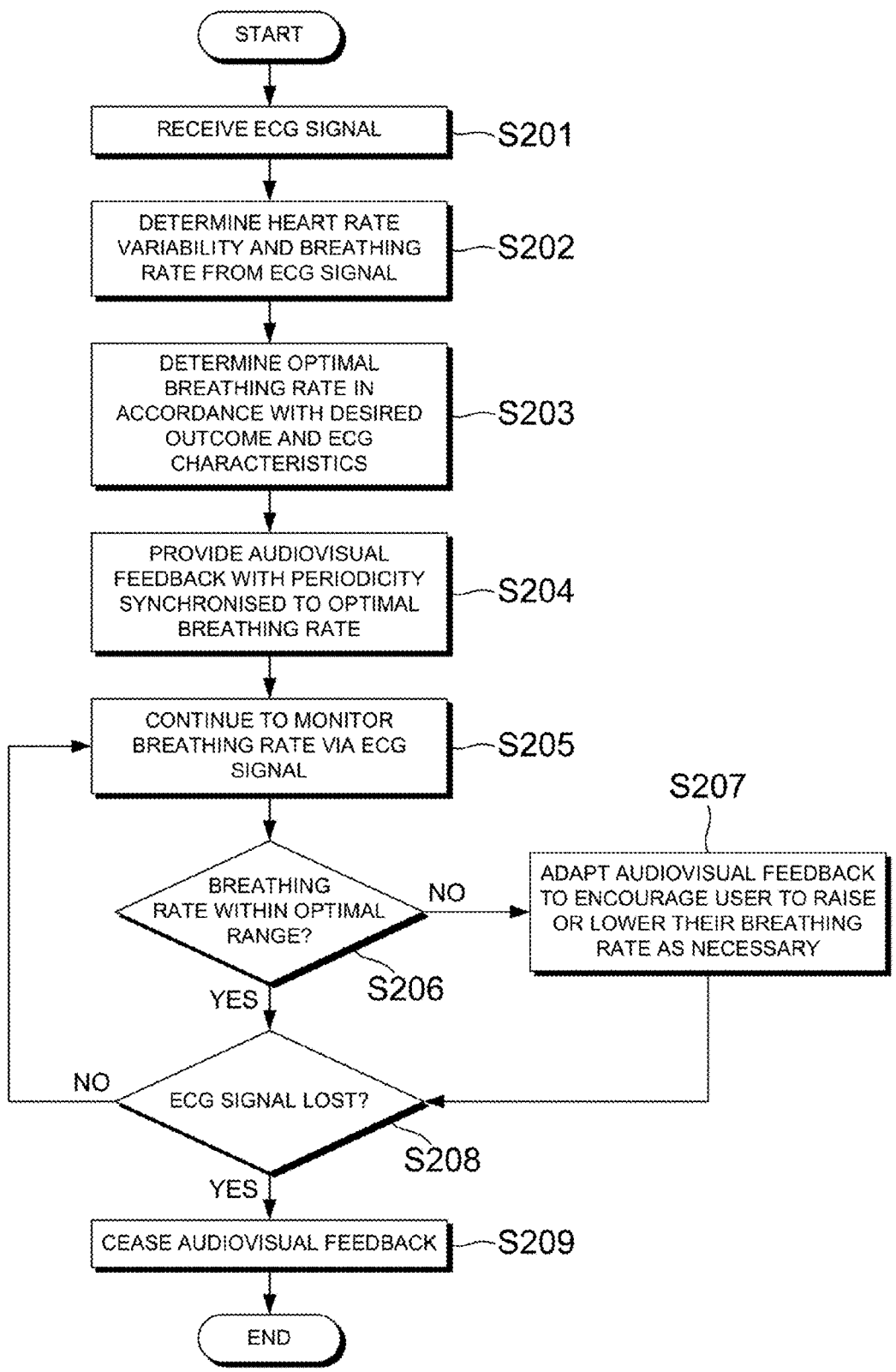
FIG. 2 is a flowchart showing a method for providing feedback regarding breathing rate, according to an embodiment.

Referring now to FIG. 2, a flowchart showing a method for providing feedback regarding breathing rate is illustrated, according to an embodiment. Depending on the embodiment, certain steps in the method may be performed locally at the device, or may be performed remotely on a server.

First, in step S201 a new ECG signal is detected when the user picks up the device and touches the ECG electrodes. Then, in step S202 the ECG analysis unit 102 obtains a breathing rate from the received ECG signal. In the present embodiment, the ECG analysis unit 102 also obtains information about HRV, as described above. Depending on the embodiment, the ECG analysis unit 102 may determine the breathing rate and/or HRV information locally, or may transmit the ECG signal to a diagnostic server and receive information about the detected breathing rate and/or HRV.

Next, in step S203 the feedback generator 103 obtains the optimal breathing rate in accordance with a desired outcome and one or more heart rate and/or breathing rate characteristics detected from the ECG signal. Depending on the embodiment, the feedback generator 103 may determine the optimal breathing rate locally or may receive the optimal breathing rate from a server.

Then, in step S204 the feedback generator 103 controls the feedback output mechanism 104 to output audiovisual feedback synchronised to the optimal breathing rate. As shown in FIG. 2, while the audiovisual feedback is being outputted, the feedback generator proceeds to continuously monitor the breathing rate via the ECG signal and subsequently adapt the audiovisual feedback in accordance with any changes detected. Specifically, in step S205 the ECG analysis unit 102 continues to monitor the breathing rate from the ECG signal, and the feedback generator 103 checks in step S206 whether the current breathing rate is within the optimal range, that is to say, within acceptable limits of the optimal breathing rate. If the breathing rate is outside the optimal range, then the feedback generator 103 adapts the audiovisual feedback as necessary in step S207 in order to encourage the user to raise or lower their breathing rate. Steps S205, S206 and S207 are repeated until the ECG signal is lost in step S208, for example when the user lets go of the device 100. Once the ECG signal is lost, the feedback generator 103 ceases to provide audiovisual feedback in step S209.

By continuously adapting the audiovisual feedback as shown in FIG. 2, the device is able to respond to changes in the user's heart rate and/or breathing rate whilst performing a breathing exercise, to keep the breathing rate within the optimal range. However, in some cases a user may not be able to perform the breathing exercise correctly. For example, a medical condition may prevent the user from achieving the optimal breathing rate. In some embodiments, the optimal breathing rate may be recalculated in response to a determination that the user is not able to achieve the optimal breathing rate. A method for determining whether the user is correctly performing the breathing exercise will now be described with reference to FIG. 3.

Figure 3:
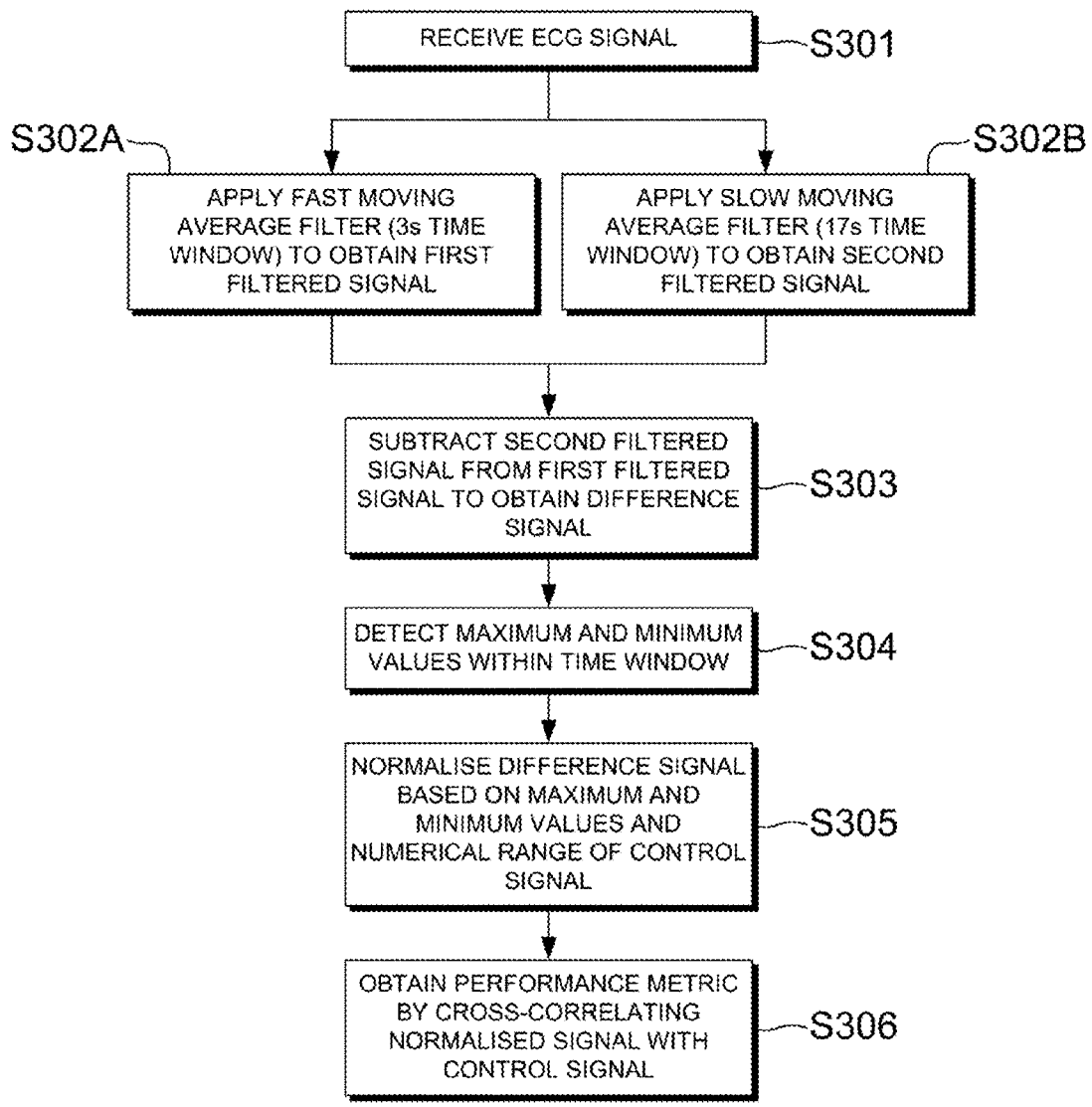
FIG. 3 is a flowchart showing a method of obtaining a performance metric related to how closely the breathing rate detected from the ECG signal is matched to the optimal breathing rate, according to an embodiment.

FIG. 3 illustrates a method of obtaining a performance metric related to how closely the breathing rate detected from the ECG signal is matched to the optimal breathing rate, according to an embodiment. In this embodiment, the feedback generator 103 is configured to generate a feedback control signal which is used to control the feedback output mechanism 104 to signal to the user when to exhale and when to inhale. The feedback generator 103 uses the feedback control signal as a reference signal to which the user's actual breathing pattern can be compared.

In the present embodiment the control signal is encoded as a continuous signal taking values between −1 and +1, with −1 corresponding to the end of the exhalation phase and +1 corresponding to the end of the inhalation phase. However, in other embodiments different upper and lower limits may be used, and the limits may correspond to other defined points in the inhalation and exhalation cycles.

First, in step S301 an ECG signal is received, and a control signal is generated according to the determined optimal breathing rate. Then, in steps S302A and S302B the feedback generator 103 is configured to obtain a first filtered signal by applying a moving average filter with a first time window to the received ECG signal, and obtain a second filtered signal by applying a moving average filter with a second time window to the received ECG signal, the second time window being longer than the first time window. The first time window is selected to filter out noise in the ECG signal, and the second time window is selected to smooth out variations within one breathing period to produce a baseline. Investigations by the inventors have shown that a first time window of substantially equal to 3 seconds (s) and a second time window of substantially equal to 17 s are optimal in most circumstances, however other values for the time windows may be used as required. The second time window should be at least as long as one breathing period, and may be adjusted as the user's breathing rate increases or decreases.

Then, in step S303 the feedback generator 103 subtracts the second filtered signal from the first filtered signal to obtain a difference between the two filtered signals. The difference signal provides information about Respiratory Sinus Arrhythmia (RSA). In step S304 determines the maximum and minimum values within a certain time window. In the present embodiment the maximum and minimum values within at least one breathing period are determined, and the time window in step S304 may be substantially equal to the second time window, for example 17 s. In some embodiments the time window in step S304 may be different to the second time window used in step S302B. For example, a longer time window could be used in step S304, although this will result in increased latency.

Next, in step S305 the difference signal is normalised relative to the control signal, based on the determined maximum and minimum values. In this way the feedback generator 103 obtains a normalised signal having values ranging from the first limit of the control signal to the second limit of the control signal. Hence in the present example the normalised signal has values between the limits of −1 and +1. Normalising the signal based on the detected maximum and minimum values ensures that the difference signal is correctly normalised, since the RSA can change from user to user.

Then, in step S306 the feedback generator 103 obtains a performance metric based on a correlation between the normalised signal and the control signal. In the present embodiment the performance metric is obtained by cross-correlating the normalised signal with the control signal. In this way, a performance metric is obtained which is related to how closely the breathing rate detected from the ECG signal is matched to the optimal breathing rate, as indicated by the control signal.

The performance metric is therefore related to the quality with which the breathing exercise is being executed by the user, and is an estimate of how synchronously RSA is reacting to the breathing exercise. RSA is a natural phenomenon that occurs with every breathing cycle. When the breathing exercise is executed correctly, that is, when a user is breathing synchronously with the audio and/or visual breathing cues provided by the audiovisual feedback, RSA will be synchronized with the control signal. As a result the cross correlation will be high. On the other hand, not following the breathing cues correctly will produce RSA that is not synchronized with the control signal, and as a result the cross correlation will be low.

The device can be configured to track the executed quality throughout the length of the breathing exercise, by regularly calculating an updated value of the performance metric. In this way the device can detect when execution quality increases or decreases, for example if the user stops following the audio and/or visual cues, or if RSA is not successfully triggered. The device is then able to adapt the visual and audio feedback by changing colour hues and the musical patterns, to illustrate to the user that the suggested breathing rate is not being followed accurately enough, and to remind them to breathe diaphragmatically instead of from the chest, whereby the effect of the breathing exercise might be reduced. The value of the performance metric may be recorded over time, and can be uploaded to a server for accessing by a healthcare professional. The performance metric can provide information about long-term trends in the user's performance in the breathing exercise, and their ability to achieve and maintain a relaxed state while using the device. In some embodiments the feedback may be adapted in accordance with the current value of the performance metric. For example, when the performance metric indicates a high execution quality, the feedback generator can be configured to include specific feedback elements as a reward (e.g. high notes), to signal to the user that the exercise is being performed correctly.

Figure 4:
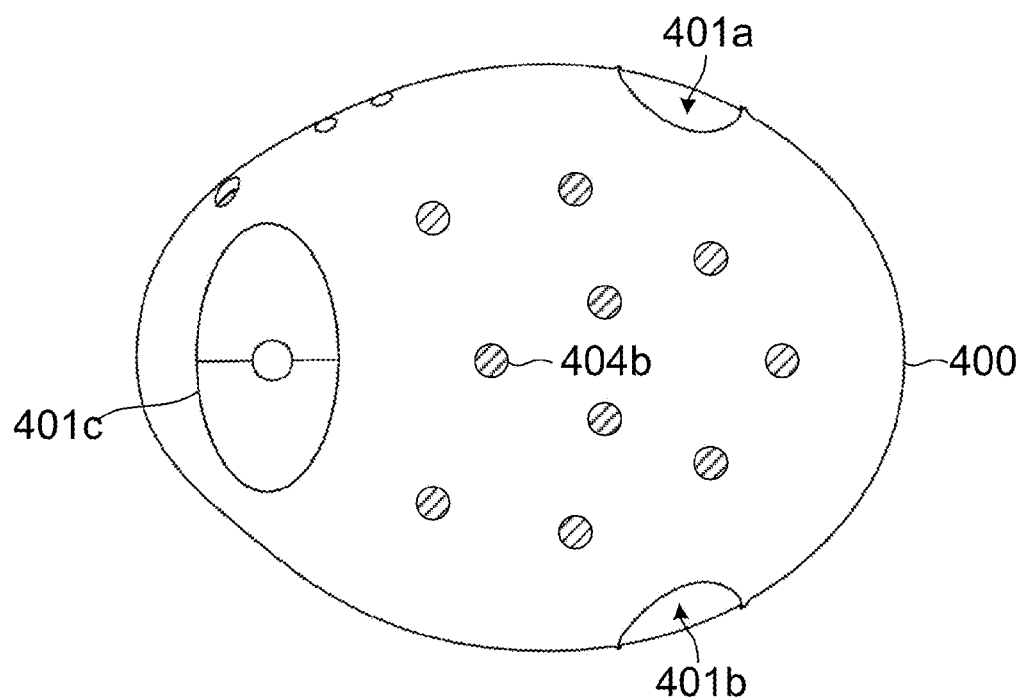
FIG. 4 illustrates a top view of a device for providing feedback regarding breathing rate, according to an embodiment.
Figure 5:
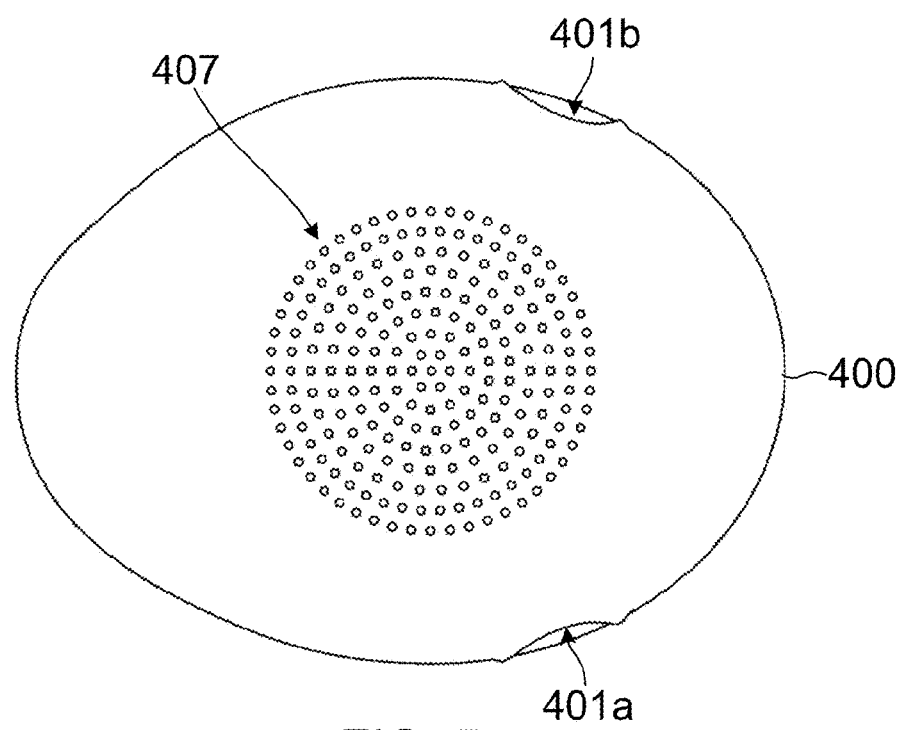
FIG. 5 illustrates a bottom view of the device of FIG. 4.
Figure 6:
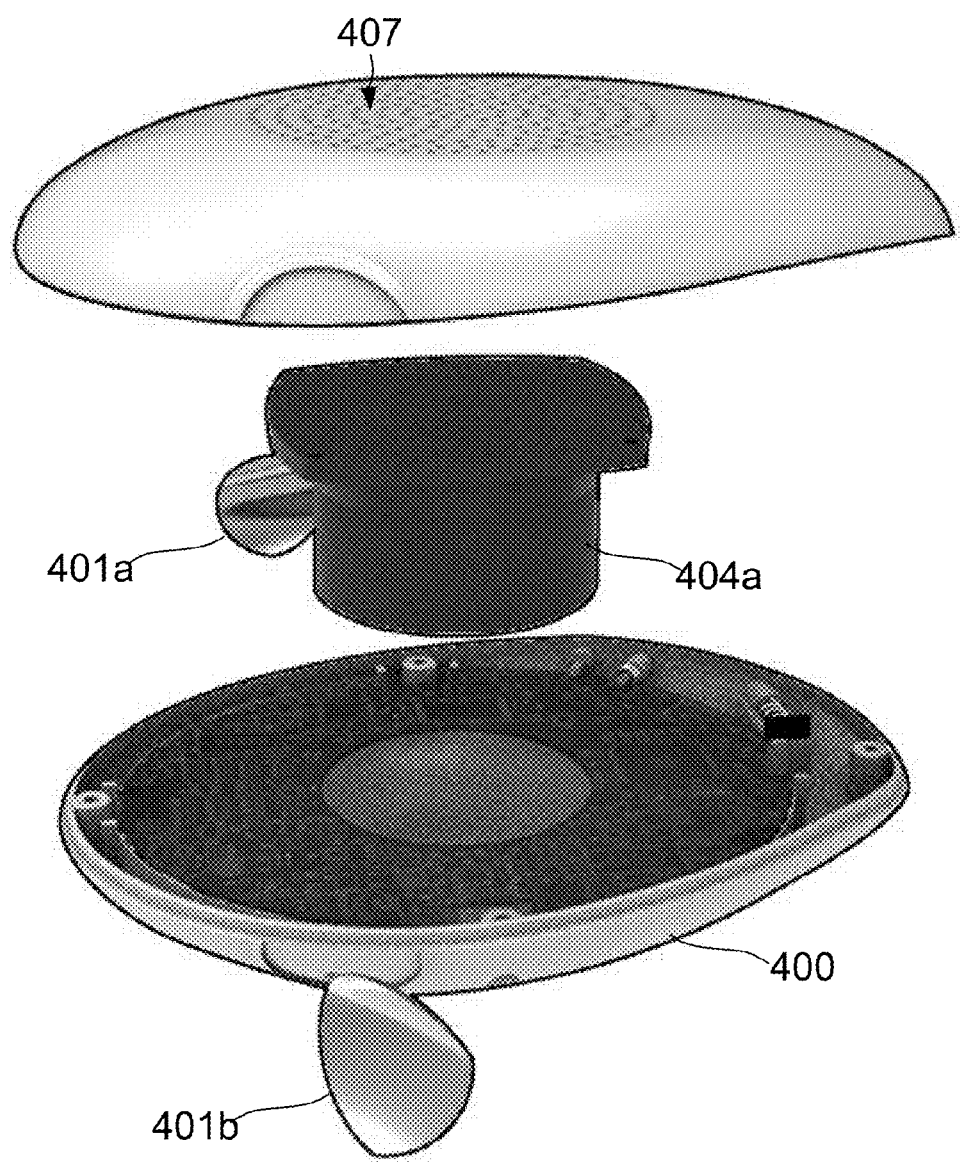
FIG. 6 illustrates an exploded view of the device of FIG. 4.

Referring now to FIGS. 4 to 6, a device for providing feedback regarding breathing rate is schematically illustrated, according to an embodiment. A top view of the device is shown in FIG. 4, a bottom view is shown in FIG. 5, and an exploded view is shown in FIG. 6. In the present embodiment, the device 400 is configured to be held and supported by a user, and includes first and second ECG electrodes 401a, 401b disposed on a surface of the device 400. The first and second ECG electrodes 401a, 401b are arranged to detect the ECG signal when the device 400 is held by a user, and in the present embodiment are disposed on opposite sides of the device 400. In addition to the first and second ECG electrodes 401a, 401b, the device 400 of the present embodiment further includes a reference ECG electrode 401c arranged to contact both hands when the device is being held by the user. The ECG analysis unit is configured to measure a reference potential from the reference ECG electrode 401c when receiving the ECG signal through the first and second ECG electrodes 401a, 401b.

Using a reference point in this way is advantageous when the device is physically connected to other electronic equipment, for example through a Universal Serial Bus (USB) cable or a power adapter. The reference electrode 401c ensures that the user is at a similar potential as the signal reference, and reduces common mode interference. However, in some embodiments the reference electrode 401c can be omitted. When the device is not electrically connected to other equipment, the reference potential is free to float at the average potential of the first and second ECG electrodes 401a, 401b.

FIGS. 4 to 6 also illustrate various components of the feedback output mechanism. As shown in FIG. 4, the feedback output mechanism of the present embodiment includes a plurality of multi-coloured LEDs 404b distributed throughout the device 400. Although LEDs are used in the present embodiment, in other embodiments different types of light source may be used, for example an LCD display may be included. In the present embodiment the LEDs 404b are disposed across an upper surface of the device 400, so as to be visible to the user when the device 400 is held in front of the body. The feedback generator can control the LEDs in order to change the colour of the device, for example to allow a gently changing glow to be created which can be soothing for the user, and help to reduce their HRV and breathing rate. Experiments carried out by the inventors have shown that a change between blue and green is relaxing for most users.

Additionally, the feedback output mechanism in the present embodiment further comprises a speaker 404a and speaker grille 407 in the body of the device 400. The speaker 404a is disposed centrally in the device 400 in order to make the device 400 easier to hold comfortably, by ensuring that the weight of the device 400 is evenly distributed between both hands. Furthermore, the speaker 404a in the present embodiment is of a sufficient size to be able to provide haptic feedback in the form of low frequency audio.

Whilst certain embodiments have been described herein with reference to the drawings, it will be understood that many variations and modifications will be possible without departing from the scope of the invention as defined in the accompanying claims.

The invention claimed is:

1. A device comprising:
a sensor interface configured to receive an electrocardiogram ECG signal;
an ECG analysis unit configured to obtain a breathing rate from the received ECG signal;
a feedback output mechanism for providing feedback; and
a feedback generator configured to obtain an optimal breathing rate in accordance with a desired outcome and one or more heart rate and/or breathing rate characteristics detected from the ECG signal, control the feedback output mechanism to output feedback synchronised to the optimal breathing rate, and subsequently adapt the feedback in accordance with changes in the one or more heart rate and/or breathing rate characteristics while the feedback is being outputted,
wherein the feedback generator is configured to generate a feedback control signal having values ranging from a first limit to a second limit, the first limit corresponding to a defined point in an exhalation phase and the second limit corresponding to a defined point in an inhalation phase,
wherein the feedback output mechanism is configured to provide the feedback in accordance with the feedback control signal, and
wherein the feedback generator is configured to:
obtain a first filtered signal by applying a moving average filter with a first time window to the received ECG signal;
obtain a second filtered signal by applying a moving average filter with a second time window to the received ECG signal, the second time window being longer than the first time window;
obtain a difference signal by subtracting the second filtered signal from the first filtered signal;
determine a maximum value and a minimum value of the difference signal within a third time window;
normalise the difference signal relative to the feedback control signal based on the determined maximum and minimum values, to obtain a normalised signal having values ranging from the first limit of the feedback control signal to the second limit of the control signal; and
obtain a performance metric based on a correlation between the normalised signal and the feedback control signal, where the performance metric is related to how closely the breathing rate detected from the ECG signal is matched to the optimal breathing rate.

2. The device of claim 1, wherein the first time window is substantially equal to 3 seconds, and/or the second time window is substantially equal to 17 seconds.

3. The device of claim 1, wherein the feedback is configured to include cues for instructing a user when to inhale and when to exhale, in accordance with the determined optimal breathing rate.

4. The device of claim 1, further comprising:
an abnormality detection mechanism configured to detect one or more predefined abnormalities based on the determined heart rate variability and/or breathing rate, and to signal a detected abnormality to the feedback generator,
wherein the feedback generator is further configured to obtain the optimal breathing rate in accordance with the detected abnormality.

5. The device of claim 4, further comprising:
a network interface for communicating with one or more other devices over a network,
wherein the abnormality detection mechanism is configured to detect the one or more predefined abnormalities by transmitting the ECG signal to a diagnostic server via the network interface and receiving a diagnostic result indicating whether any of the predefined abnormalities were detected in the ECG signal.

6. The device of claim 1, further comprising:
a network interface for communicating with one or more other devices over a network,
wherein the ECG analysis unit is configured to obtain the breathing rate by transmitting the ECG signal to a server via the network interface, and receiving a message containing the detected breathing rate via the network interface, and/or
wherein the feedback generator is configured to obtain the optimal breathing rate by querying a server via the network interface.

7. The device of claim 1, wherein the feedback output mechanism comprises:
a plurality of light sources distributed across the device, the plurality of light sources being controllable to emit visible light of different wavelengths in accordance with the generated feedback.

8. The device of claim 1, wherein the feedback output mechanism comprises:
a speaker for outputting an audio component of the generated feedback, and
wherein the feedback generator is further configured to control the speaker to provide haptic feedback in the form of low-frequency audio.

9. The device of claim 1, configured to be held and supported by a user, wherein the sensor interface comprises:
first and second electrocardiographic electrodes disposed on a surface of the device, the first and second electrocardiographic electrodes being arranged to detect the ECG signal when the device is held by the user.

10. The device of claim 9, further comprising:
a third electrocardiographic electrode arranged to contact both hands when the device is being held by the user, wherein the ECG analysis unit is configured to measure a reference potential from the third electrocardiographic electrode when receiving the ECG signal through the first and second electrocardiographic electrodes.

11. The device of claim 1, wherein the ECG analysis unit is configured to determine the breathing rate as being equal to a variation in peak amplitude of a pulse detected from the ECG signal.

12. A method comprising:
receiving an electrocardiogram ECG signal;
obtaining a breathing rate from the received ECG signal;
obtaining an optimal breathing rate in accordance with a desired outcome and one or more heart rate and/or breathing rate characteristics detected from the ECG signal;
controlling a feedback output mechanism to output feedback synchronised to the optimal breathing rate, wherein the feedback is provided in accordance with a feedback control signal having values ranging from a first limit to a second limit, the first limit corresponding to a defined point in an exhalation phase and the second limit corresponding to a defined point in an inhalation phase;
subsequently adapting the feedback in accordance with changes in the one or more heart rate and/or breathing rate characteristics while the feedback is being outputted;
obtaining a first filtered signal by applying a moving average filter with a first time window to the received ECG signal;
obtaining a second filtered signal by applying a moving average filter with a second time window to the received ECG signal, the second time window being longer than the first time window;
obtaining a difference signal by subtracting the second filtered signal from the first filtered signal;
determining a maximum value and a minimum value of the difference signal within a third time window;
normalising the difference signal relative to the feedback control signal based on the determined maximum and minimum values, to obtain a normalised signal having values ranging from the first limit of the feedback control signal to the second limit of the control signal; and
obtaining a performance metric based on a correlation between the normalised signal and the feedback control signal, where the performance metric is related to how closely the breathing rate detected from the ECG signal is matched to the optimal breathing rate.

13. A non-transitory computer-readable storage medium on which is stored computer program instructions which, when executed, perform the method according to claim 12.

* * * * *